US009366736B2

(12) United States Patent
Cho et al.

(10) Patent No.: US 9,366,736 B2
(45) Date of Patent: Jun. 14, 2016

(54) SEALED MAGIC ANGLE SPINNING NUCLEAR MAGNETIC RESONANCE PROBE AND PROCESS FOR SPECTROSCOPY OF HAZARDOUS SAMPLES

(71) Applicants: Herman M. Cho, Richland, WA (US); Nancy M. Washton, Richland, WA (US); Karl T. Mueller, Richland, WA (US); Jesse A. Sears, Jr., Kennewick, WA (US); Mark R. Townsend, Kennewick, WA (US); R. James Ewing, Kennewick, WA (US)

(72) Inventors: Herman M. Cho, Richland, WA (US); Nancy M. Washton, Richland, WA (US); Karl T. Mueller, Richland, WA (US); Jesse A. Sears, Jr., Kennewick, WA (US); Mark R. Townsend, Kennewick, WA (US); R. James Ewing, Kennewick, WA (US)

(73) Assignee: BATTELLE MEMORIAL INSTITUTE, Richland, WA (US)

( * ) Notice: Subject to any disclaimer, the term of this patent is extended or adjusted under 35 U.S.C. 154(b) by 336 days.

(21) Appl. No.: 14/106,441

(22) Filed: Dec. 13, 2013

(65) Prior Publication Data
US 2014/0167756 A1    Jun. 19, 2014

Related U.S. Application Data

(60) Provisional application No. 61/736,935, filed on Dec. 13, 2012.

(51) Int. Cl.
*G01V 3/00* (2006.01)
*G01R 33/30* (2006.01)
*G01N 24/08* (2006.01)
*G01R 33/465* (2006.01)

(52) U.S. Cl.
CPC .............. *G01R 33/307* (2013.01); *G01R 33/30* (2013.01); *G01N 24/08* (2013.01); *G01N 24/084* (2013.01); *G01R 33/465* (2013.01)

(58) Field of Classification Search
CPC ........................................................ G01R 33/30
USPC ........................................ 324/321, 318, 322
See application file for complete search history.

(56) References Cited

U.S. PATENT DOCUMENTS

| | | | |
|---|---|---|---|
| 5,221,903 A * | 6/1993 | Kasten et al. ................. | 324/321 |
| 7,075,303 B2 * | 7/2006 | Cavaluzzi et al. ............ | 324/321 |
| 8,106,657 B2 * | 1/2012 | Sakellariou et al. .......... | 324/321 |
| 2007/0018646 A1 | 1/2007 | Hoath | |

OTHER PUBLICATIONS

Cho, H., et al., Probing the oxygen environment in UO22+ by solid-state 17O nuclear magnetic resonance spectroscopy and relativistic density functional calculations, The Journal of Chemical Physics, 132, 2010, 084501.
Farnan, I. et al., Quantification of actinide a-radiation damage in minerals and ceramics, Nature, 445, 2007, doi:10.1038/nature 05425, 190-193.
Felmy, A. R., et al., The aqueous complexation of thorium with citrate under neutral to basic conditions, Radiochim. Acta, 94, 2006, 205-212.

(Continued)

*Primary Examiner* — Louis Arana
(74) *Attorney, Agent, or Firm* — James D. Matheson

(57) ABSTRACT

A magic-angle-spinning (MAS) nuclear magnetic resonance (NMR) probe is described that includes double containment enclosures configured to seal and contain hazardous samples for analysis. The probe is of a modular design that ensures containment of hazardous samples during sample analysis while preserving spin speeds for superior NMR performance and convenience of operation.

15 Claims, 13 Drawing Sheets

(56) References Cited

OTHER PUBLICATIONS

Wang, Z., et al., Complexation of Cm(III)/Eu(III) with silicates in basic solutions, Radiochim. Acta, 93, 2005, 741-784.

Farnan, I., et al., High-resolution solid-state nuclear magnetic resonance experiments on highly radioactive ceramics, Review of Scientific Instruments, 75, 12, 2004, 5323-5326.

Cho, H., et al., Temperature and Isotope Substitution Effects on the Structure and NMR Properties of the Pertechnetate Ion in Water, J. Am. Chem. Soc., 126, 2004, 11583-11588.

Cho, H., et al., Comprehensive Solid-State NMR Characterization of Electronic Structure in Ditechnetium Heptoxide, J. Am. Chem. Soc., 132, 2010, 13138-13140.

\* cited by examiner ified pellet. The sample may be analyzed within
SEALED MAGIC ANGLE SPINNING NUCLEAR MAGNETIC RESONANCE PROBE AND PROCESS FOR SPECTROSCOPY OF HAZARDOUS SAMPLES

CROSS REFERENCE TO RELATED APPLICATION

This is a Non-Provisional application that claims priority from U.S. Provisional Application No. 61/736,935 entitled "Sealed NMR Probe for Spectroscopy of Hazardous Solids", filed 13 Dec. 2012, which application is incorporated in its entirety herein.

STATEMENT REGARDING RIGHTS TO INVENTION MADE UNDER FEDERALLY-SPONSORED RESEARCH AND DEVELOPMENT

This invention was made with Government support under Contract DE-AC05-76RLO1830 awarded by the U.S. Department of Energy. The Government has certain rights in the invention.

FIELD OF THE INVENTION

The present invention relates generally to magic-angle-spinning (MAS) nuclear magnetic resonance (NMR) probes. More particularly, the present invention relates to a magic angle spinning probe that includes double containment compartments that provides containment of hazardous sample materials.

BACKGROUND OF THE INVENTION

Magic Angle Spinning (MAS) is a scientific technique that enhances resolution of NMR spectra acquired on solid, semi-solid, and mixed samples. Conventional MAS-NMR probes typically have open designs that facilitate loading and removal of samples. The term "open" means the stator assembly is not sealed within an enclosure or isolated such that it has a separate atmosphere from that positioned exterior to the probe. That is, the interior and exterior atmospheres are continuous. The open design allows direct venting of gases to the environment or atmosphere exterior to the probe during operation that are used to spin, and regulate temperature of, the sample. Electrical connections are also facilitated by an open, accessible layout. However, while convenient, the open architecture of conventional probes precludes analyses of hazardous samples including, e.g., radioactive samples and hazardous chemical and biological samples. Such samples must be isolated to protect the laboratory environment exterior to the probe, to protect individuals from contamination, or to otherwise protect the sample. NMR data from radioactive samples is of interest to researchers involved in development of nuclear waste forms, environmental remediation, nuclear medicine, and fundamental electronic structure theory. Technical challenges when analyzing radioactive solids include ensuring complete, secure containment of samples exposed to flows of high pressure gases while simultaneously preserving ease of operation and minimizing impacts to NMR instrument performance. Sample spinning requires large volumes of high pressure (>50 psi) gas to spin rotors containing the sample. Under conditions of high gas flows, dispersal of hazardous sample particulates can occur through leaks in, or failure of, the rotor. Accordingly, new probe designs are needed that ensure complete containment of hazardous samples that prevent dispersal of sample particulates that also preserve ease of operation and functional capabilities for high-resolution measurements. The present invention addresses these needs.

SUMMARY OF THE INVENTION

The present invention includes a sealable Magic Angle Spinning (MAS) Nuclear Magnetic Resonance (NMR) probe configured with a magnetically shielded probe body with a primary (inner) containment enclosure and a secondary (outer) containment enclosure. The probe body may include or be constructed of a conducting metal that shields internal electrical circuits and components from electromagnetic radiation that can interfere with MAS NMR measurements during operation. The MAS-NMR probe with the sealed inner enclosure and sealed outer enclosure provides double containment and isolation of hazardous samples from the exterior environment during analyses while allowing high-pressure gases to flow into the stator assembly in the inner enclosure to suspend and spin the rotor containing the hazardous sample. The probe simultaneously filters exhaust gases exiting from the stator assembly and out of the device, thus preventing dispersal of contaminating particles. The present invention also maintains spinning performance, temperature control, sensitivity, power handling, ease of operation, and superior NMR performance all while providing secure containment of the hazardous samples.

In various applications, hazardous samples may include, but are not limited to, e.g., radioactive materials, biological materials, chemical materials, and combinations of these various materials. In various applications, samples may be in the form of solids and/or semi-solids. In some applications, samples may be in the form of a powder. In some applications, samples may be in the form of a pellet such as a monolithic pellet.

The present invention also includes a method for sealing hazardous samples for MAS NMR analysis. The rotor containing the hazardous sample or another sample may be introduced into a stator assembly within the MAS NMR probe. The inner (first) enclosure may be sealed to contain the hazardous sample or other sample within the stator assembly. The inner enclosure may be secured to the base platform to form a first containment volume within the inner containment enclosure. The base platform may be positioned beneath the inner enclosure. The outer enclosure may be sealed by securing the outer enclosure to the probe body to form a secondary containment volume within the probe. The outer enclosure prevents release of sample particulates within the probe in the event of a breach in the rotor or the inner enclosure during operation. The rotor containing a hazardous sample may be spun in a stator assembly located within a Contamination Area or other controlled environment external to the probe to ensure that the hazardous sample is properly sealed in the rotor before introducing the sample into the sealable MAS NMR probe for analysis. The sample may be analyzed within the sealed MAS NMR probe to collect RF signal data for analysis of the sample. Following analysis, the rotor containing the hazardous sample may be removed from the stator assembly within the inner enclosure into a Contamination Area or other controlled environment to exchange the hazardous sample or other samples for analysis.

The MAS NMR probe of the present invention is of a modular design that may include a lower module and an upper module. The probe may include an electrically shielded probe body. The upper module may include a primary or inner enclosure (containment compartment) and a secondary or outer enclosure (containment compartment) each with separate containment volumes when sealed. The secondary enclosure may extend into the lower module of the probe body. The modular design allows the inner enclosure in the upper module containing the hazardous sample to be separated from the outer enclosure and remaining probe structures and components without breaching the sealed containment volume of the inner enclosure containing the hazardous sample when needed to allow for convenient cleanup, disposal, and/or contamination surveys.

The inner enclosure may be secured to a base platform positioned within the inner enclosure. The inner (primary) enclosure when secured to the base platform seals the inner containment volume which encloses a stator assembly with a rotor containing the hazardous sample or another sample for analysis. Sealing the inner enclosure may include mounting a collar over a flange positioned at the base end of the inner enclosure and threading the collar onto inner threads that circumvolve the base platform. The collar may compress a seal that seals the inner enclosure and the primary containment volume, which isolates the hazardous sample within the inner enclosure of the MAS NMR probe.

The outer enclosure when secured to the probe body isolates the inner enclosure preventing release of the hazardous sample in the event of a breach in the inner enclosure or release of the hazardous sample within the MAS NMR probe. Sealing the secondary enclosure may include mounting a collar over a flange positioned at the base end of the outer enclosure and threading the collar onto external threads located on the probe body. The collar may compress a seal that seals the outer enclosure and the secondary containment volume, which isolates the hazardous sample within the inner enclosure of the MAS NMR probe. Sealing the outer enclosure may also include attaching a viewport made of a transparent polycarbonate to the outer enclosure after introducing the hazardous sample within the inner enclosure. The viewport allows viewing of the inner enclosure during analysis.

In the event of a rotor failure, double containment provided by the inner enclosure and the outer enclosure prevents dispersal of sample particulates outside of the containment volume. The MAS NMR probe is also configured to prevent release of the samples to the exterior laboratory environment and to isolate the exterior laboratory environment from the samples during operation.

The containment system of the present invention includes a securely filtered exit port that vents high-pressure gases used to drive sample spinning. The sealed inner enclosure of the present invention also allows samples to be maintained in an inert atmosphere during MAS NMR experiments unlike conventional NMR probes with open architectures.

The inner enclosure (containment compartment) may be constructed of a polished polycarbonate that allows viewing of the stator assembly and the inner containment volume during analysis of the hazardous sample when the inner enclosure is sealed. The inner enclosure may secure to a base platform in the upper module of the probe body. The inner enclosure may include a collar that secures to the base platform to provide a gas-tight seal for encapsulation of the sample material within the inner enclosure during MAS NMR measurements. Removing the inner enclosure from the base platform provides access to the stator assembly for exchange of samples.

The outer enclosure may include a containment cap that includes or is comprised of a transparent polycarbonate that attaches to the top end of the outer enclosure. The containment cap allows the inner containment volume containing the hazardous sample to be viewed during operation of the probe.

The containment cap is removable and when removed provides ready access to the inner enclosure for exchange of samples from the stator assembly therein.

The sealed MAS NMR probe includes filters that filter hazardous particles from gas streams or ambient air. Filters in the probe body provide a particle removal rating of at least 99.999999% at a size down to 0.003 μm (microns) or better at a maximum flow rate of 225 standard liters per minute. Other filters may be selected. The sealed MAS NMR probe with leak-proof connections and seals does not impact spinning performance.

The sealed sample inner enclosure (compartment) can maintain a sample in a controlled and/or inert atmosphere during MAS NMR experiments. Contamination Areas and other controlled environments may include a negative pressure glovebox or a laminar flow fume hood.

The MAS NMR probe of the present invention may include one or more RF tuning circuits that may be mounted, e.g., to a radiofrequency deck positioned within the lower module. Each RF tuning circuit may include variable or fixed capacitors and an inductor that couple electrically via electrical conductors to the stator assembly within the inner enclosure. The RF circuits allow tuning of selected resonant frequencies of the probe during analysis of the hazardous samples or other samples. The stator assembly of the MAS NMR probe may be configured to transmit and receive radiofrequency (RF) NMR signals in selected and/or different frequency bands simultaneously. In some applications, the probe may be configured with up to three or more resonant frequency bands simultaneously.

The probe may include a tachometer connector that couples to a tachometer cable or other fiber optic cable. The tachometer cable or other fiber optic cable may couple operatively to the stator assembly within the inner enclosure to measure and regulate rotational speed of the MAS NMR rotor during analysis of hazardous samples.

The probe may include one or more gas delivery conduits including a bearing gas conduit and a drive (spin) gas conduit configured to deliver high-pressure gases through a base platform into the inner enclosure for rotation of the rotor containing the hazardous sample or other sample during operation when the inner enclosure is sealed. The gas delivery conduits may be coupled to one or more in-line check valves configured to prevent release of sample particulates due to overpressures or gas backflows during analysis of hazardous samples within the inner enclosure when sealed. The inner enclosure may include one or more exhaust gas conduits. At least one gas exhaust conduit may be configured to remove high pressure exhaust gases from the inner enclosure without releasing containment of the hazardous sample during operation of the MAS NMR probe. Exhaust gas conduits may be configured to release high-pressure exhaust gases from the stator assembly through the base platform in the upper module that ensure that the spin speed of the stator assembly is preserved during operation without releasing containment in the inner enclosure when sealed. Exhaust gas conduits may be coupled to one or more particulate filters positioned, e.g., within the lower module of the probe body to remove sample particulates from the exhaust gas in the event of a release of sample particulates from the inner enclosure.

The purpose of the foregoing abstract is to enable the United States Patent and Trademark Office and the public generally, especially the scientists, engineers, and practitioners in the art who are not familiar with patent or legal terms or phraseology, to quickly determine the nature and essence of the technical disclosure of the application. The abstract is neither intended to define the invention of the application, which is measured by the claims, nor is it intended to be limiting as to the scope of the invention in any way. Accordingly, drawings and descriptions of the preferred embodiment set forth hereafter are to be regarded as illustrative in nature, and not restrictive. A more complete appreciation of the invention will be readily obtained by reference to the following description of the accompanying drawings in which like numerals in different figures represent the same structures or elements. The foregoing summary is neither intended to define the invention, which is defined by the claims, nor to be limiting as to the scope of the invention in any way.

DETAILED DESCRIPTION

A Magic Angle Spinning (MAS) Nuclear Magnetic Resonance (NMR) probe is described of a double containment design that provides secure containment of hazardous samples during MAS-NMR operation and analysis. The MAS-NMR probe may also be used to collect MAS-NMR measurements for non-hazardous samples having sufficient $B_1$ field amplitudes, decoupling strengths, spinning stabilities, sensitivities, and/or resolution. The MAS-NMR probe addresses shortcomings of conventional open sample area designs that cannot secure nor analyze various hazardous sample materials. In the following description, embodiments of the present invention are shown and described by way of illustration of the best mode contemplated for carrying out the invention. It will be clear from the following description that the invention is susceptible of various modifications and alternative constructions. The present invention covers all modifications, alternative constructions, and equivalents falling within the spirit and scope of the invention as defined in the claims. Therefore the description should be seen as illustrative and not limiting.

Figure 1A:
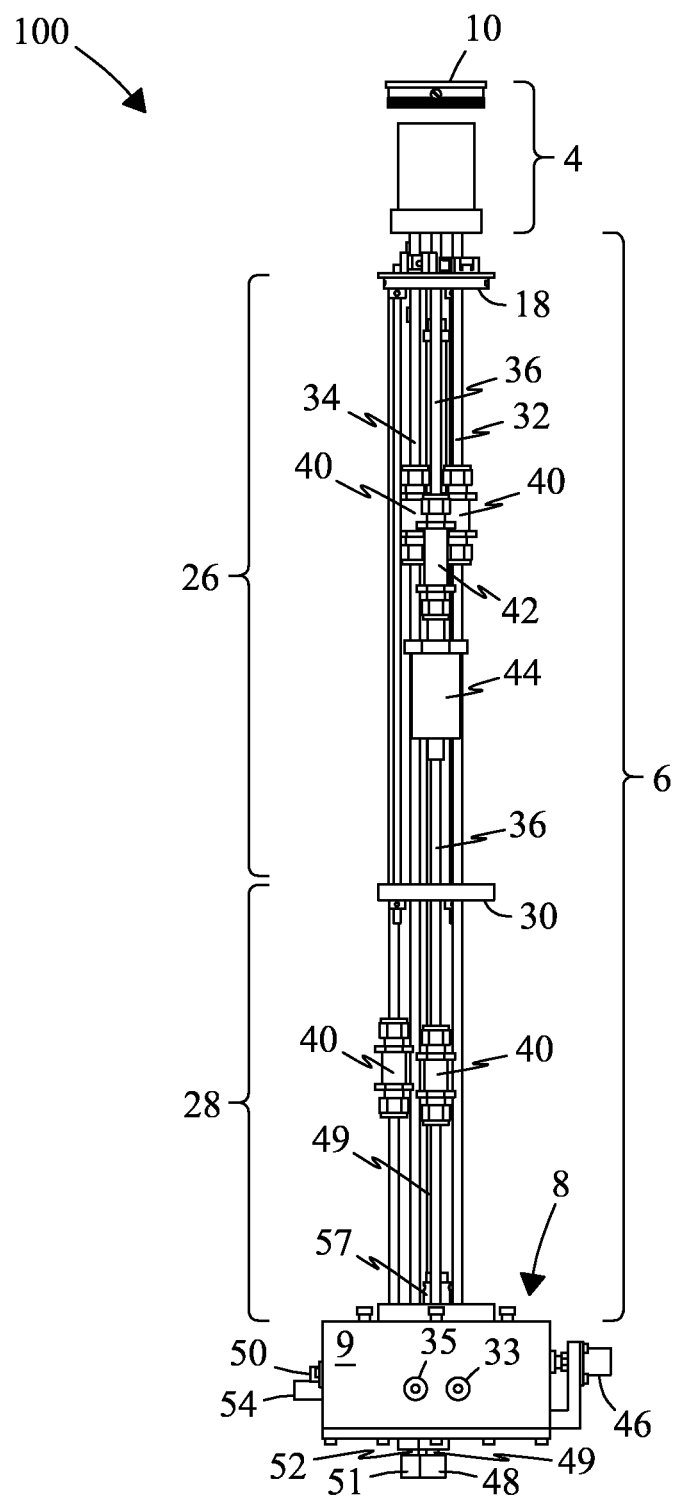
FIGS. 1A-1C are schematics showing various perspective views of the MAS-NMR probe of the present invention.
Figure 1B:
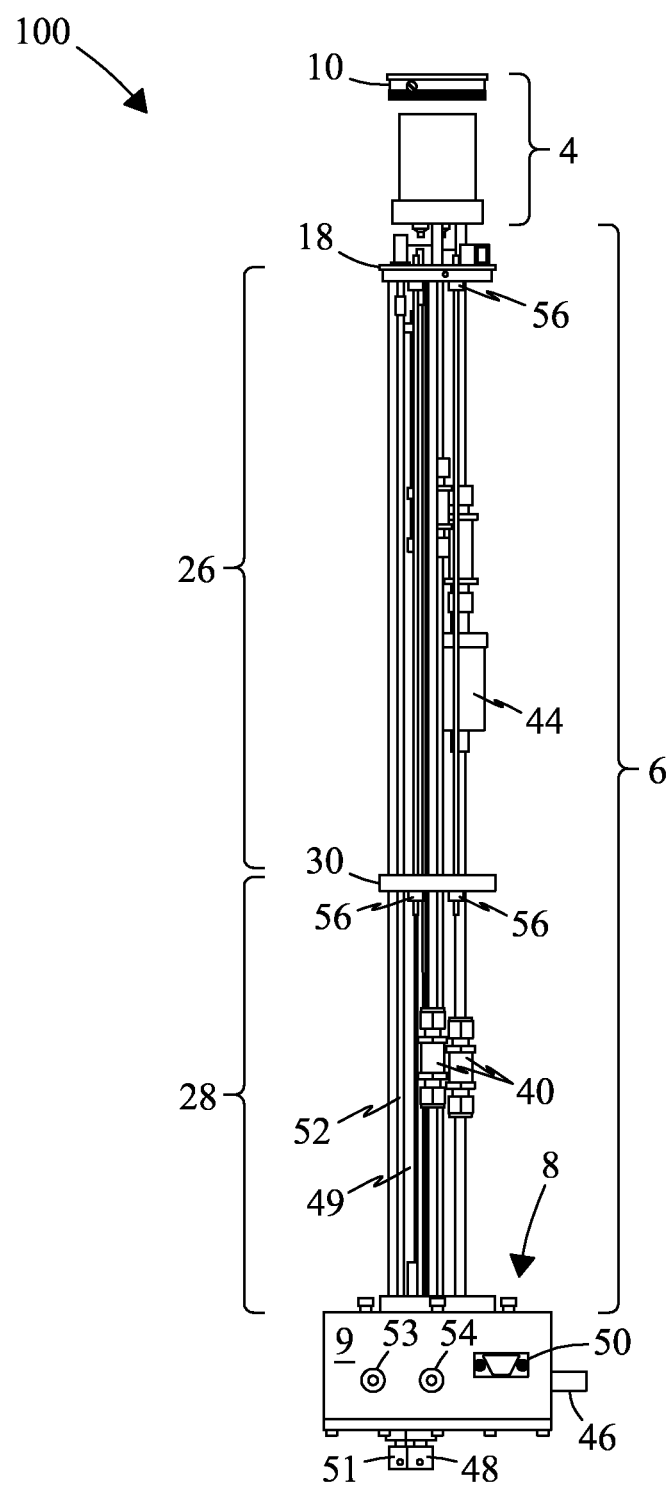

FIGS. 1A-1B show components and inner architecture of MAS-NMR probe 100. In the exemplary embodiment, MAS-NMR probe 100 may include an upper module ("probe head") 4 and a lower module 6, and a probe base 8. Upper module 4 includes an inner or primary enclosure (not shown) and an outer or secondary enclosure (not shown) for containment of hazardous samples during analysis, described further in reference to FIG. 2. Probe 100 is of a design that allows upper module 4 to be opened so that hazardous samples may be easily introduced (i.e., loaded) and removed in a designated contamination area or controlled area such as a fume hood coupled to high-efficiency particulate filters or other containment zone that allows for convenient cleanup and surveys for contamination. In the unlikely event of a breach in sample containment during operation (i.e., samples dispersed or otherwise not recoverable from the inner enclosure), the modular design allows the inner enclosure (described further in reference to FIGS. 2A-2B) in its sealed configuration on the base platform (FIG. 2A-2B) to be separated from lower module 6, permitting proper disposal or disposition of the hazardous materials.

A containment cap (viewport) 10 that includes or is constructed of a transparent polycarbonate or other suitable transparent material may attach to the top of upper module 4 to allow viewing of enclosures within upper module 4 without opening the containment.

Electrical components for detecting NMR signals may be mounted to a radiofrequency deck (platform) 18 positioned in lower module 6 immediately below upper module 4, as detailed further herein in reference to FIG. 3.

Figure 2A:
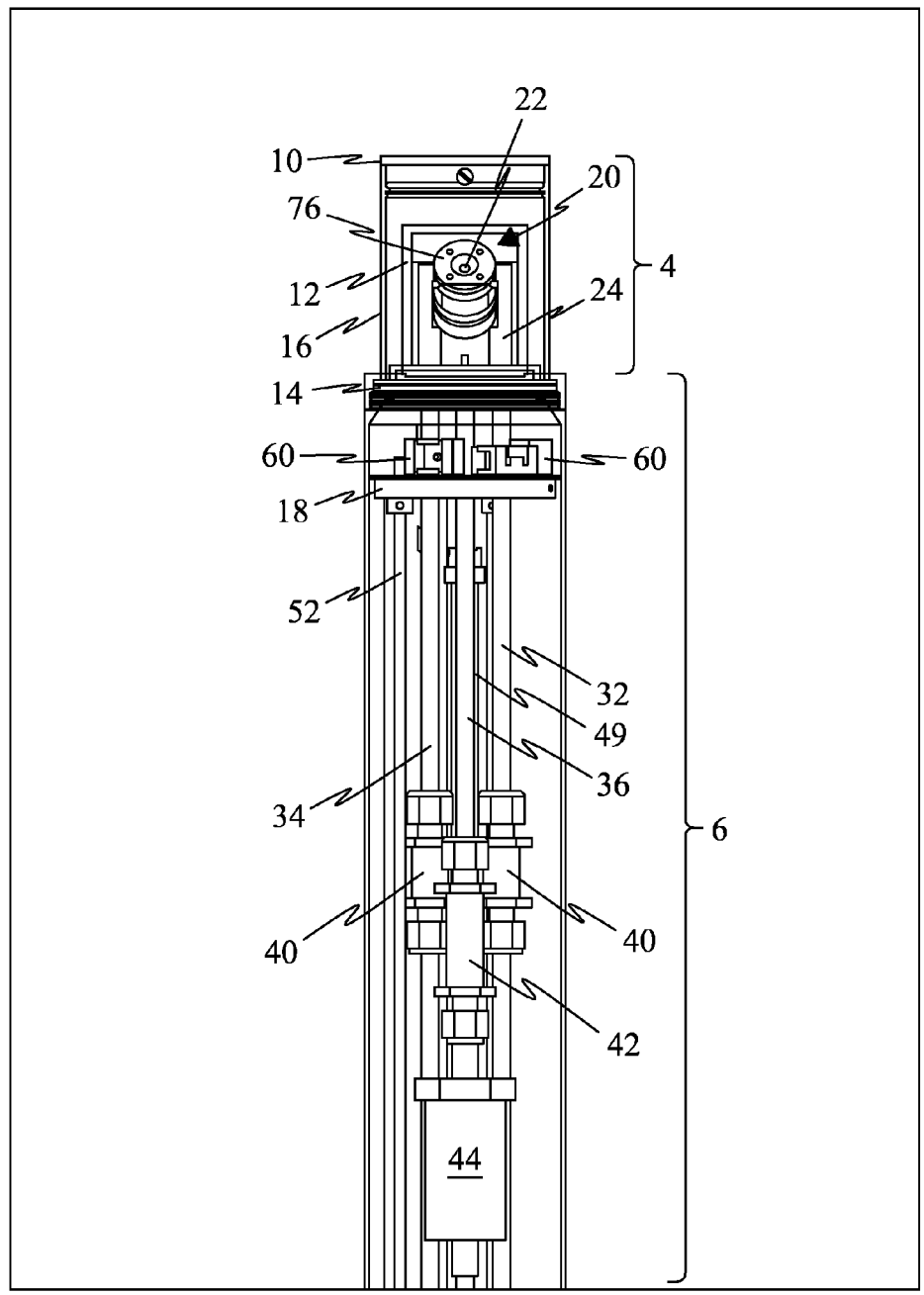
FIG. 2A shows the upper module and lower module in the assembled MAS NMR Probe.

Lower module 6 may include an upper extension section 26 and a lower extension section 28 with a bridge (divider) 30 positioned between upper extension section 26 and lower extension section 28. Divider 30 provides structural integrity and ensures support of extension sections 26 and 28 within lower module 6. Upper extension section 26 and lower extension section 28 contain various gas transfer conduits (tubes) 32 and 34 that deliver high-pressure gases to and from the stator assembly (FIG. 2A) in inner enclosure (FIG. 2A).

Upper extension section 26 and lower extension section 28 of lower module 6 may include check valves 40 introduced at various positions along the length of individual high pressure gas-delivery conduits (tubes) 32 and 34 in lower module 6 that prevent back flow of high-pressure gases within gas-delivery conduits 32 and 34 should over-pressurization occur within the inner enclosure of upper module 4. Position and number of check valves is not limited.

Upper extension section 26 may also include one or more particulate air filters 42 and 44 that filter exhaust gases returning from upper module 4. Position and number of particulate air filters is not limited.

Probe base 8 may include one or more gas valves or ports for introducing high-pressure gases into the probe or for venting high-pressure exhaust gases from the probe. In the exemplary embodiment, probe base 8 may include a drive gas port 33 that introduces a high-pressure drive gas into the drive gas conduit 32 that spins the sample rotor within the upper module 4. Probe base 8 may also include a bearing gas port 35 that introduces a high-pressure bearing drive gas into the bearing gas conduit 34 that suspends the rotor within the upper module 4.

Probe base 8 may further include one or more RF connectors 46 that transmit radiofrequency electrical currents to and from the stator assembly (FIG. 2A) containing the sample.

Probe base 8 may include a tachometer connector 50 that couples to a tachometer cable (not shown) for determining and/or recording speed of rotation of the MAS NMR probe 100 during sample analysis.

Probe base 8 may also include a purge gas connector 54 that penetrates through probe base cover 9 into probe base 8 to deliver high-pressure purge gas into lower module 6 described further herein.

Probe base 8 may also include a tuning rod adjustment knob 48 that couples to a tuning rod 49 within probe base 8. Probe base 8 may also include a matching rod adjustment knob 51 that couples to a matching rod 52 within probe base 8. In the exemplary embodiment, tuning rod 49 and matching rod 52 span the length of lower module 6 and couple to the variable capacitor (FIG. 3) of the H-channel circuit (FIG. 3) mounted on radiofrequency deck 18. Tuning rod 49 allows manual adjustment of resonance frequencies of the probe electrical circuits. Matching rod 52 manually adjusts impedances of electrical circuits of probe 100 that enhance sensitivity for MAS NMR measurements.

Figure 1C:
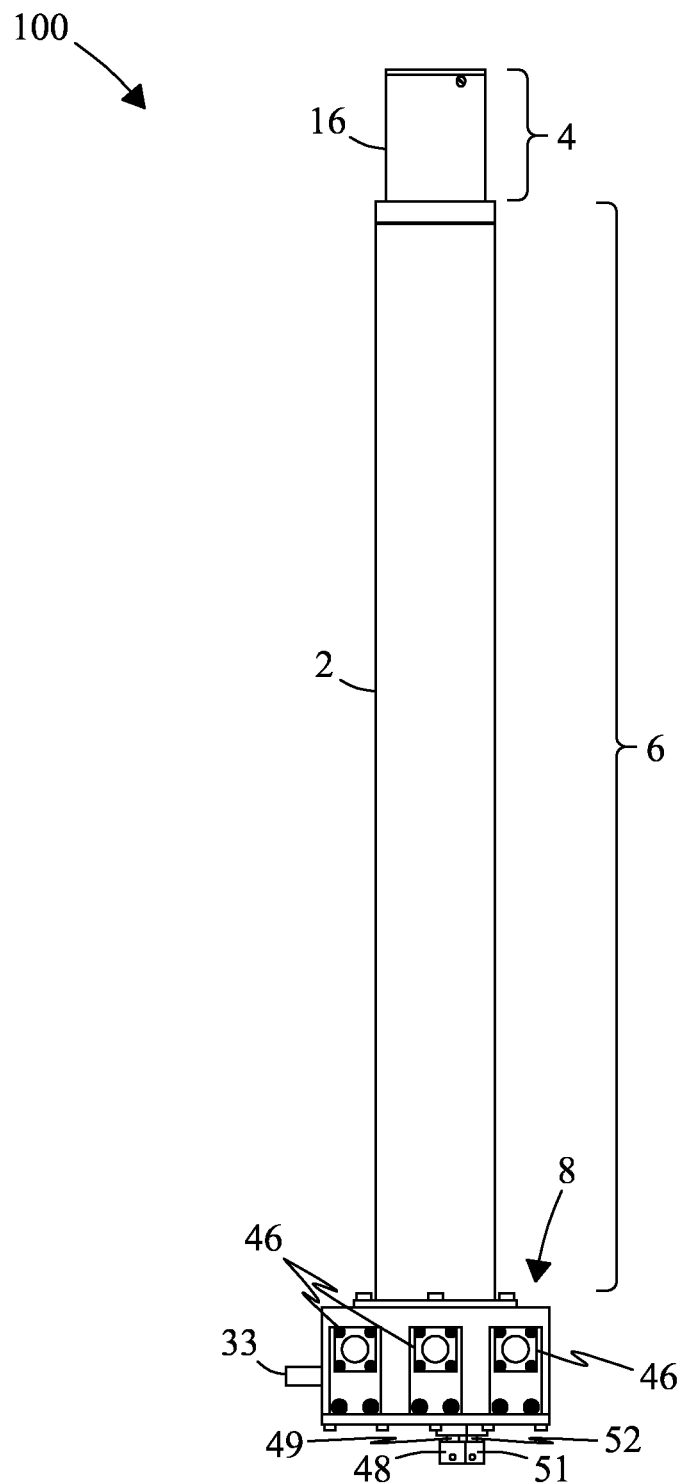

FIG. 1C shows the shielded housing 2 of the fully assembled MAS-NMR probe 100. Shielded housing 2 of probe 100 may include or be constructed of a conducting metal such as aluminum or other conducting material that provides electrical shielding of internal electronic components described hereafter in reference to FIGS. 2A-2B and FIG. 3. During assembly, upper module 4 with sealed outer enclosure (FIGS. 2A-2B) and sealed inner enclosure (FIGS. 2A-2B) secures to lower module 6. Upper module 4 and lower module 6 with their respective components then insert into the shielded metal housing (probe body) 2. Probe body 2 may then be secured to probe base 8, e.g., with locking screws (not shown) or another securing device.

Figure 3:
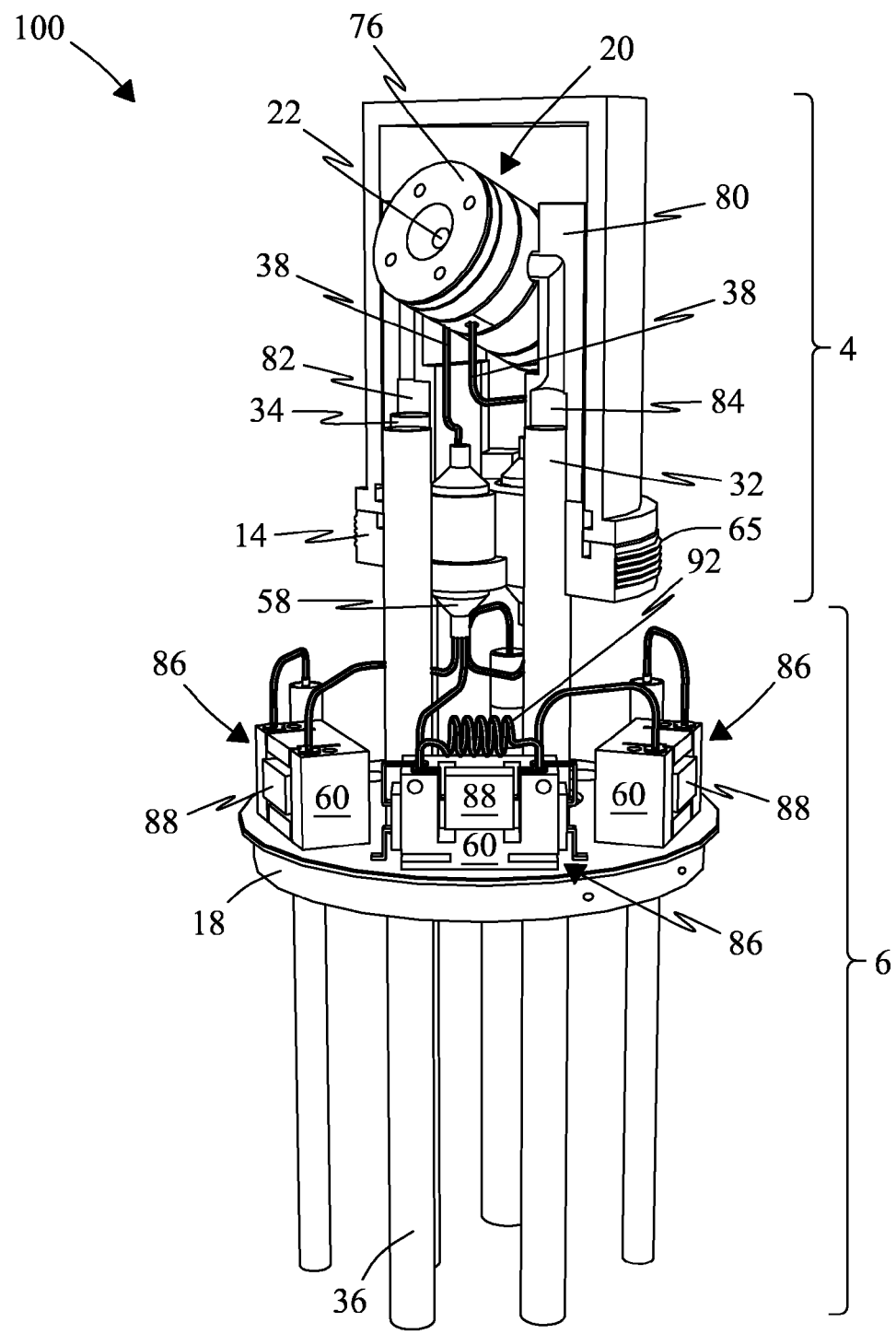
FIG. 3 shows electrical and spinning components of the MAS-NMR probe for analyzing hazardous samples in accordance with the present invention.

In the figure, probe base 8 may include one or more RF connectors 46 that link to selected RF circuits discussed further in reference to FIG. 3 via coaxial cables (not shown) positioned within lower module 6. In the exemplary embodiment, RF connectors 46 may be of a sealed bulkhead design and attach to probe base 8 with, e.g., four machine screws.

Probe base 8 may further include one or more gas inlet ports or valves or gas exhaust ports or valves. In the figure, probe base 8 includes a drive gas inlet port 33.

In the figure, a tuning rod 49 is shown attached to a tuning rod adjustment knob 48. A matching rod 52 is shown attached to a matching rod adjustment knob 51 (described previously in reference to FIGS. 1A-1B), which are detailed further herein in reference to FIG. 4A.

All components as will be selected by those of ordinary skill in the spectroscopic art in view of this disclosure are within the scope of the present invention. No limitations are intended.

FIG. 2A shows a cut away view of upper module 4 and lower module 6 in the assembled and sealed MAS-NMR Probe 100. Upper module 4 includes an inner enclosure 12 and an outer enclosure 16. A stator assembly 20 mounts to base platform 14 and is so positioned so as to be fully enclosed within inner enclosure 12 during sample analyses. Stator assembly 20 includes a rotor housing 76 with a sample loading chamber 22 that is configured to receive and spin an MAS rotor (not shown) containing the sample material therein. Stator assembly 20 also includes a detector (not shown) for acquiring NMR signals from samples loaded within the sample rotor.

Outer enclosure 16 and inner enclosure 12 secure to a base platform 14 positioned immediately below inner enclosure 12 and outer enclosure 16. Inner enclosure 12 provides leak-proof connections that seal and isolate hazardous samples during analyses. When secured to base platform 14, outer enclosure 16 provides secondary sample containment that isolates and prevents release of hazardous sample particulates in the event of a breach of inner enclosure 12 or release of sample material from the sample rotor during operation of probe 100. Together, inner enclosure 12 and outer enclosure 16 provide double containment of hazardous sample materials during MAS NMR spectroscopic analyses. Sealing of inner enclosure 12 does not impact spinning performance of stator assembly 20.

In the figure, outer enclosure 16 may include a transparent polycarbonate containment cap (viewport) 10 that attaches at the top of upper module 4 to allow viewing of the sample containment area and stator assembly 20 within inner enclosure 12 during operation.

Probe 100 further includes a lower module 6 positioned beneath base platform 14. Various electrical components for tuning frequencies of the MAS NMR probe during samples analyses may be mounted to a radiofrequency deck 18 positioned in lower module 6 immediately below base platform 14.

High-resolution NMR analyses of solid samples typically require a flow of large volumes of gas at high pressures (>50 psi) to spin rotors containing the sample. Under conditions of high gas flows, dispersal of hazardous sample particulates can occur through failure of, or leaks in, the rotor. Lower module 6 of the MAS-NMR probe 100 includes conduits (tubes) constructed of selected metals, metal alloys, or other suitable high-pressure materials with selected dimensions that deliver high-pressure gases to and from inner enclosure 12 in upper module 4. In the exemplary embodiment, lower module 6 may include a drive or spin gas delivery conduit 32 that delivers high-pressure gas that spins the sample rotor within stator assembly 20 for analysis. A bearing gas delivery conduit 34 may deliver high-pressure gas that suspends the rotor within stator assembly 20 prior to sample spinning. An exhaust gas conduit 36 serves to return high-pressure exhaust gas released from inner enclosure 12 from upper module 4. Exhaust gas conduit 36 maintains the proper high gas pressures needed to spin the rotor so that the sealed inner enclosure 12 does not impact spinning performance of stator assembly 20.

Drive gas conduit 32 and bearing gas conduit 34 may include one or more in-line check valves 40 that prevent back flow of high-pressure gases in the event of over-pressure conditions in inner enclosure 12. Gas exhaust tube 36 may include one or more in-line filters 42 and 44 that prevent escape of hazardous sample particles if released from the sample containment area (volume) 62 within inner enclosure 12. Filters may be selected to remove hazardous sample particulates from high-pressure gas streams or ambient air passing through probe during sample analysis that directly cleans gas contaminates. In the exemplary embodiment, exhaust tube 36 may include an in-line pre-filter 42 (e.g., a model SS-6F-15 filter, Swagelok, Solon, Ohio, USA) as a primary filter and a high-efficiency filter 44 (e.g., a model SS-SCF3-VR4-P-225 filter, Swagelok, Solon, Ohio, USA) as a final filter that in combination provide a particulate removal rating greater than 99.999999% at a particle size down to 0.003 µm (microns) at a maximum gas flow rate of 225 standard liters (L) per minute (L/min). Filters and filter materials are not intended to be limited.

Figure 2B:
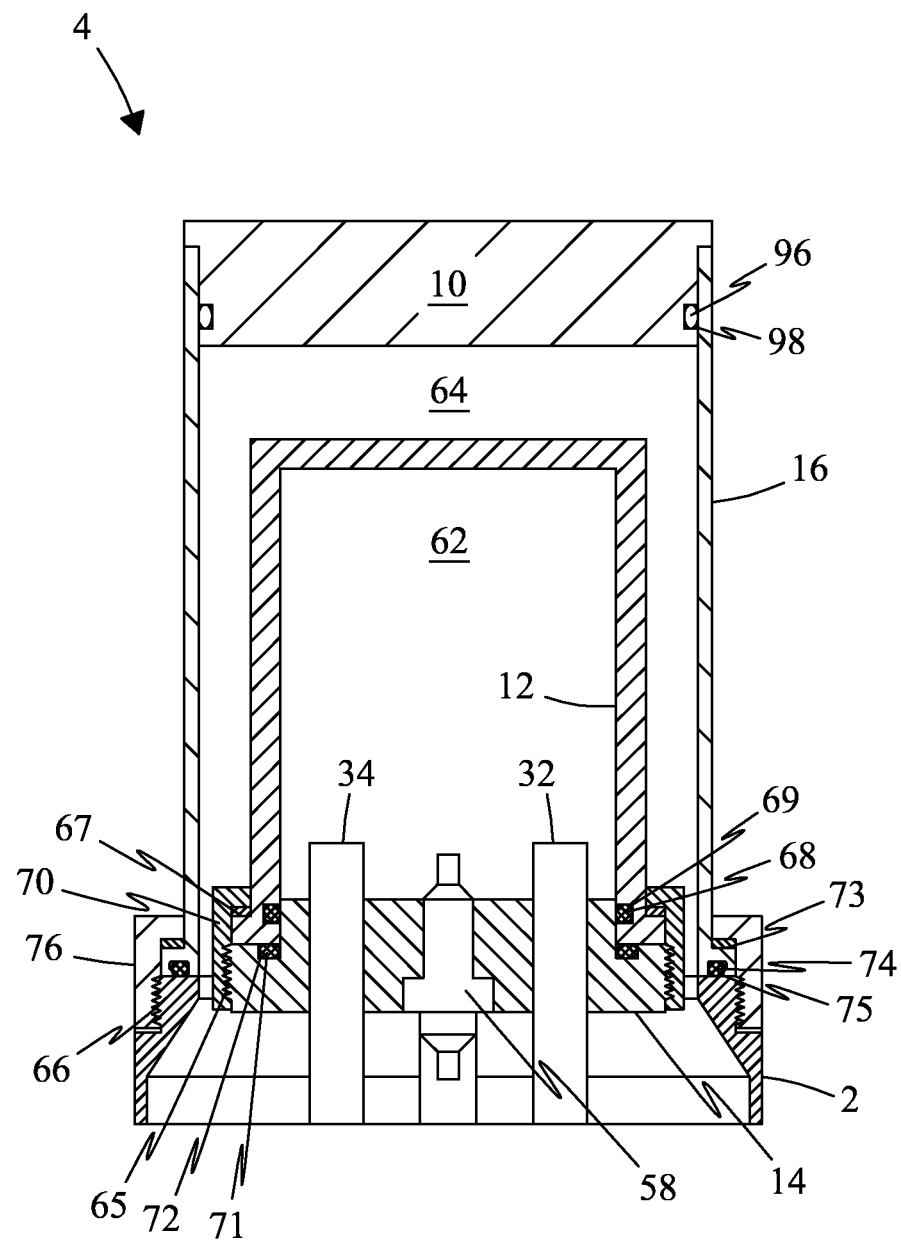
FIG. 2B is a cross-sectional view of the upper module in the assembled MAS NMR Probe.

FIG. 2B is a cross-sectional view of the upper module 4 showing the thread configuration for securing inner enclosure 12 and outer enclosure 16 within the MAS NMR probe. Inner enclosure 12 and outer enclosure 16 include respective containment volumes 62 and 64 that encapsulate hazardous samples in the rotor within inner enclosure 12 isolating the hazardous samples from the exterior environment.

Outer enclosure 16 may be constructed of a conducting material such as aluminum metal that shields components within probe 100 from electrical interference that can cause analysis errors during operation. Outer enclosure 16 may include a transparent polycarbonate containment cap (viewport) 10 that secures at the top of outer enclosure 16. Containment cap 10 may include an O-ring (seal) 96 introduced within a groove 98 positioned along the inner wall at the top of outer enclosure 16, which seals outer enclosure 16 and prevents release of hazardous samples in the event of a breach in inner enclosure 12.

Inner enclosure 12 is preferably constructed of a transparent material such as polished polycarbonate to allow viewing of the sample containment area (volume) 62 and stator assembly (FIG. 2A) within inner enclosure 12 through containment cap (viewport) 10 during operation.

In the exemplary embodiment, inner enclosure 12 and outer enclosure 16 of upper module 4 are of a threaded design that secure to base platform 14. Base platform 14 may include one or more threaded surfaces including superior (top-most) inner threads 65 that circumvolves base platform 14. Lower exterior threads 66 may be positioned on the probe body 2 at the top end of lower module 6 below inner threads 65 on base platform 14.

Inner enclosure 12 may include an upper O-ring 68 introduced into a groove 69 located between the top (superior) end of base platform 14 and the inner wall at the base (sealing) end of inner enclosure 12. Inner enclosure 12 may also include a flange 67 that sits atop a crush O-ring 71 introduced into a groove 72 directly under flange 67. A threaded inner collar 70 constructed of brass or another suitable material mounts over the top of crush O-ring 71 and screws onto inner threads 65. O-ring 71 seals inner enclosure 12 when inner enclosure 12 is secured to base platform 14 over the top of stator assembly (see FIG. 2a), which encloses and seals the stator assembly within inner enclosure 12.

Outer enclosure 16 may include a flange 73 that sits atop a crush O-ring 74 positioned within a groove 75 on base platform 14. A threaded outer collar 76 constructed of brass or another suitable material may mount over the top of outer enclosure 16 and screw onto lower exterior threads 66 over the top of flange 73 compressing crush O-ring 74, which secures and seals outer enclosure 16 to base platform 14. When secured over the top of inner enclosure 12, outer enclosure 16 provides secondary containment of hazardous samples introduced within inner enclosure 12.

In the unlikely event of a breach in inner enclosure 12 or a release of hazardous samples from the rotor during operation of the MAS-NMR probe 100, outer enclosure 16 prevents dispersal of hazardous samples outside the sample containment area (volume) 62 of inner enclosure 12. The modular design of probe 100 allows inner enclosure 12 with contained sample materials to be separated from lower module (FIG. 1A) providing convenient disposal and disposition of hazardous sample materials. Disposition of hazardous sample materials permits cleanup and surveys for contamination. When sealed, inner enclosure 12 within probe 100 maintains samples in a controlled or inert atmosphere during MAS NMR measurements.

In the figure, a bearing gas conduit 34 and spin gas conduit 32 penetrate through base platform 14 and provide high-pressure gases into the stator assembly (not shown) within inner enclosure 12. A feedthrough 58 positioned in base platform 14 allows co-axial cable conductors to be introduced into inner enclosure 12 to carry NMR signals to and from the stator assembly, as described further in reference to FIG. 3.

Tuning and Spinning Components

FIG. 3 shows selected tuning and spinning components in MAS-NMR probe 100 for analysis of hazardous samples. In the figure, stator assembly 20 is enclosed within inner (primary) enclosure 12 in upper module 4. Stator assembly 20 includes a rotor housing 76 and a rotor loading chamber 22 (described previously in reference to FIG. 2A) that receives the sample rotor (not shown) containing the sample for sample analysis. Stator assembly 20 also includes a receiver coil (not shown) that surrounds the rotor when introduced into sample chamber 22 in stator assembly 20. Stator assembly 20 mounts to an air post 80 positioned on base platform 14. A bearing gas duct 82 and a drive (spin) gas duct 84 deliver high-pressure gases to stator assembly 20. Bearing gas duct 82 couples to a bearing gas delivery conduit (tube) 34 in lower module 6 that delivers the bearing gas through a feed-through (not shown) in base platform 14 to bearing gas duct 82 and ultimately into stator assembly 20. Drive gas duct 84 couples to a drive gas delivery conduit (tube) 32 in lower module 6 that delivers high-pressure drive gas through a feed-through (not shown) in base platform 14 into stator assembly 20 that turns the sample rotor (not shown) when introduced into rotor loading chamber 22 in stator assembly 20. An exhaust gas conduit 36 delivers high-pressure gases exiting stator assembly 20 down through lower module 6 and out through the probe base (FIG. 4a) to exit from MAS-NMR probe 100.

In the exemplary embodiment, probe 100 includes a radiofrequency tuning deck 18 constructed of brass or another suitable material positioned in lower module 6 immediately below base platform 14 for mounting tuning components [except for the receiver coil]. Tuning components include, but are not limited to, e.g., tuning circuits 86 and radiofrequency tuning cables or conductors 38. In the figure, a conductor feedthrough 58 positioned through base platform 14 introduces radiofrequency cables (conductors) 38 through penetrations (not shown) in base platform 14 from lower module 6 into inner enclosure 12 in upper module 4 that deliver NMR signals to and from stator assembly 20 during operation. Penetrations may be completely sealed with a sealing material such as epoxy. Conductor feed-through 58 may be surrounded by an insulator material (e.g., a TEFLON® insulator) to prevent shorting between conductors 38 and base platform 14. Radiofrequency cables 38 may connect at one end to stator assembly 20 in inner enclosure 12 and at the other end to tuning circuits 86 mounted to radiofrequency deck 18. In the preferred embodiment, conductors 38 form part of the removable inner enclosure 12 which may be separated from lower module 6.

In the figure, MAS-NMR probe 100 may include three resonant tuning circuits 86 termed $^1$H, X, and Y that allow probe 100 to be tuned to three radiofrequency bands simultaneously. Tuning circuits 86 provide a desired tuning range, quality factor, and power-handling capability. Components and features of tuning circuits are described, e.g., by Fukushima and Roeder in *Experimental Pulse Nuclear Magnetic Resonance: A Nuts and Bolts Approach* (Addison-Wesley, New York, 1981), which reference is incorporated herein. Tuning circuits 86 may include fixed and variable tuning capacitors 88 including, e.g., $^1$H-channel capacitors, X-channel capacitors, and Y-channel capacitors that may be mounted into respective RF circuit holders 60. Resonant frequencies selected are proportional to the magnetic field strength. As such, the following description is exemplary only, and not limiting. In the exemplary embodiment, for example, the $^1$H-channel circuit may span a frequency range delimited by the $^{19}$F (705.6 MHz) isotope and the $^3$H isotope (800 MHz). The X and Y channel circuits may span frequencies of the $^{13}$C isotope (188.6 MHz) to the $^{31}$P isotope (303.6 MHz) and from the $^{14}$N isotope (54.2 MHz) to the $^{29}$Si isotope (149.0 MHz), respectively. Tuning circuits 86 may also include tuning coils (inductors) 92 that provide electrical isolation of the $^1$H, X, and Y circuits.

Sealing within MAS-NMR Probe

Figure 4A:
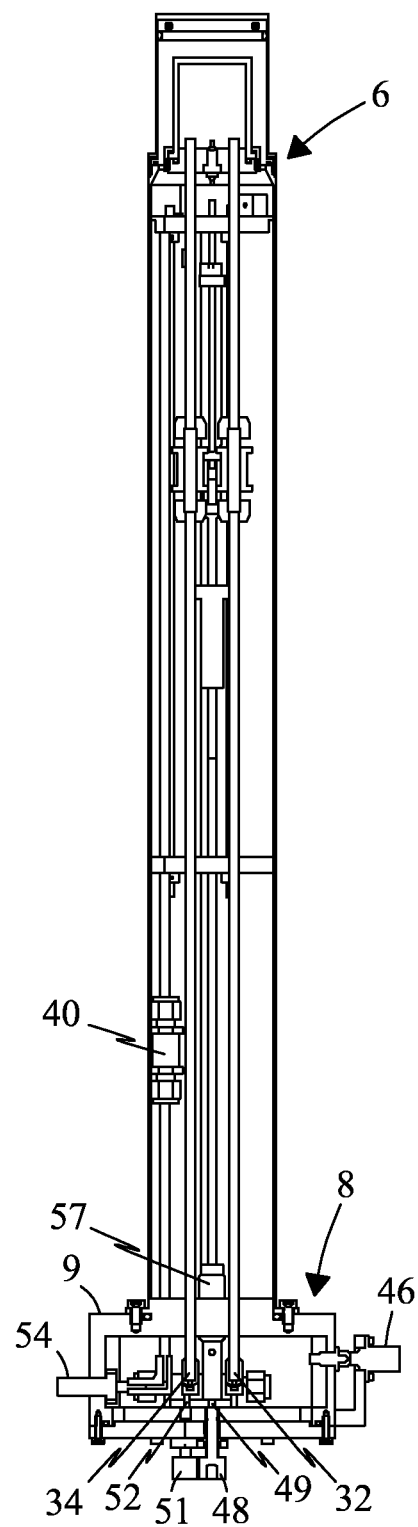
FIGS. 4A-4F show expanded views of seals positioned along the length of the MAS NMR probe.

FIG. 4A is a cross sectional view of probe base 8 showing external and internal components. Valves and ports described herein for the MAS NMR probe of the present invention may be sealed with O-ring seals, gasket seals, or other sealing devices to prevent release of hazardous particle-containing gases. In the figure, probe base 8 includes a probe base cover 9 that covers internal components within probe base 8. A purge gas connector 54 (described previously in reference to FIGS. 1A-1B) with sealed penetrations may penetrate through probe base cover 9 into probe base 8 to deliver high-pressure purge gas into lower module 6. One or more RF connectors 46 (described previously in reference to FIGS. 1A-1B) may be attached to probe base cover 9 with sealed penetrations that penetrate into probe base 8. A tuning rod adjustment knob 48 may extend through the bottom of probe base cover 9 and connect to a tuning rod 49 positioned within probe base 8. Tuning rod 49 may extend through a tuning rod feed-through 57 in probe base 8 into the lower module (FIGS. 1A-1B) through the top of probe base cover 9 ultimately coupling with variable capacitors (FIG. 3) that tune tuning circuits of MAS NMR probe 100. A matching rod adjustment knob 51 may extend through the bottom of probe base cover 9 and connect with a matching rod 52 positioned within probe base 8. Matching rod 52 may extend through a matching rod feed-through (not shown) positioned within probe base 8 through the top of probe base cover 9 into the lower module (FIGS. 1A-1B) ultimately coupling with variable capacitors (FIG. 3) that adjusts impedances to enhance sensitivity of MAS NMR probe 100.

In the figure, probe base 8 includes a drive gas inlet port 33 and a bearing gas inlet port (not shown) that deliver high-pressure gases into lower module 6 for operation of the stator assembly (FIG. 2A) positioned within the inner enclosure at the top end of the MAS NMR probe described previously in reference to FIGS. 1A-1B.

Figure 4B:
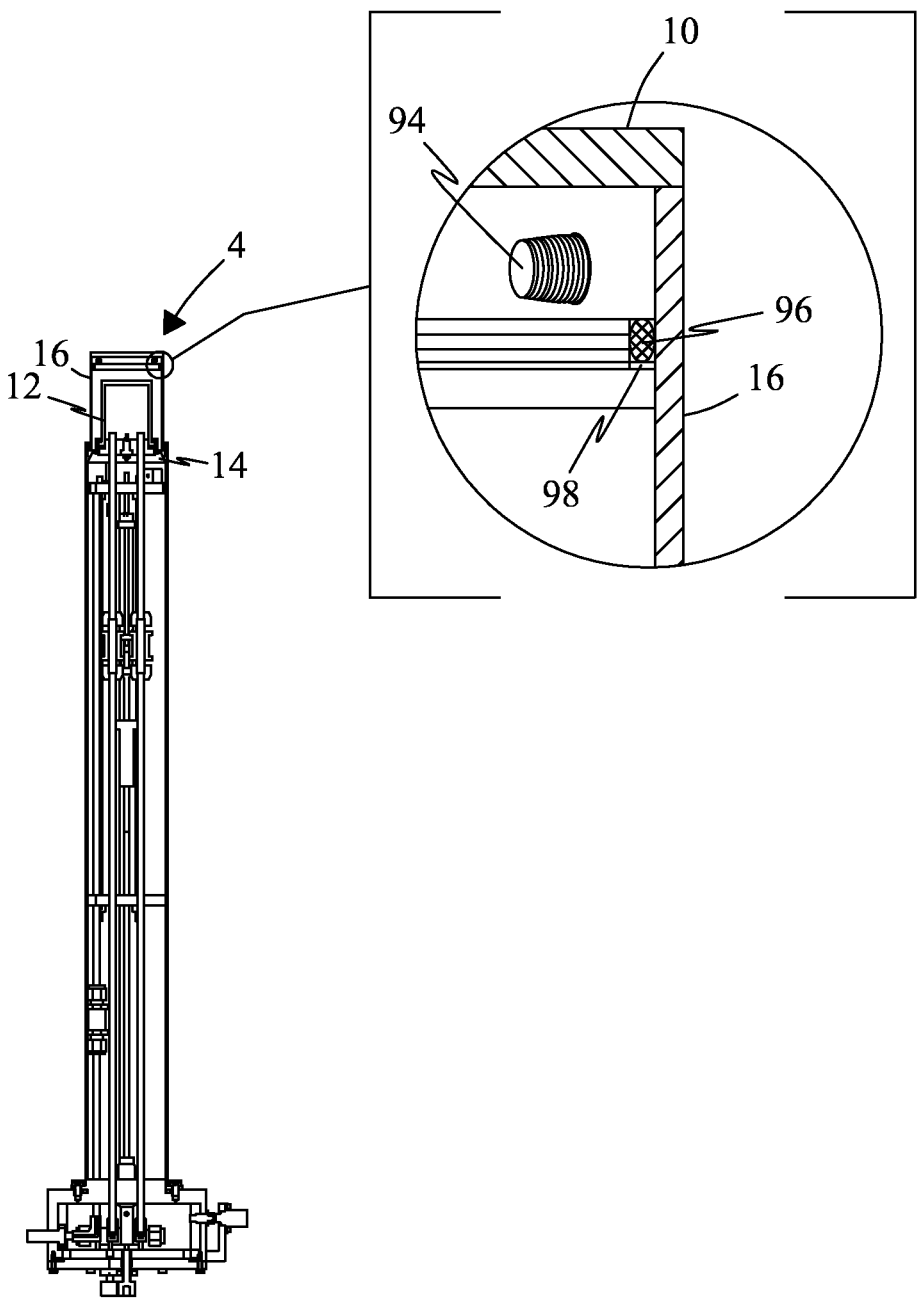

FIG. 4B shows an expanded side view of the clear polycarbonate cap (viewport) 10 (described previously in reference to FIG. 2B) positioned at the top end of outer enclosure 16 within upper module 4. Cap (viewport) 10 when attached to the top of outer enclosure 16 serves to enclose inner enclosure 12 when secured and sealed to base platform 14. In the exemplary embodiment, cap (viewport) 10 has a shape of a shallow cup which inserts upside down inside the aluminum shielding of outer enclosure 16. Aluminum shielding (of outer enclosure 16) may be secured to cap 10, e.g., with brass screws 94 (e.g., 3 screws) that thread into screw holes (not shown) introduced into, and positioned 120° apart around, aluminum shielding of outer enclosure 16. In the figure, an O-ring seal 96 may be positioned within a groove 98 located between the interior wall of the aluminum shielding of outer enclosure 16 and the exterior wall of viewport 10 below screws 94 (described previously in reference to FIG. 2B).

Figure 4C:
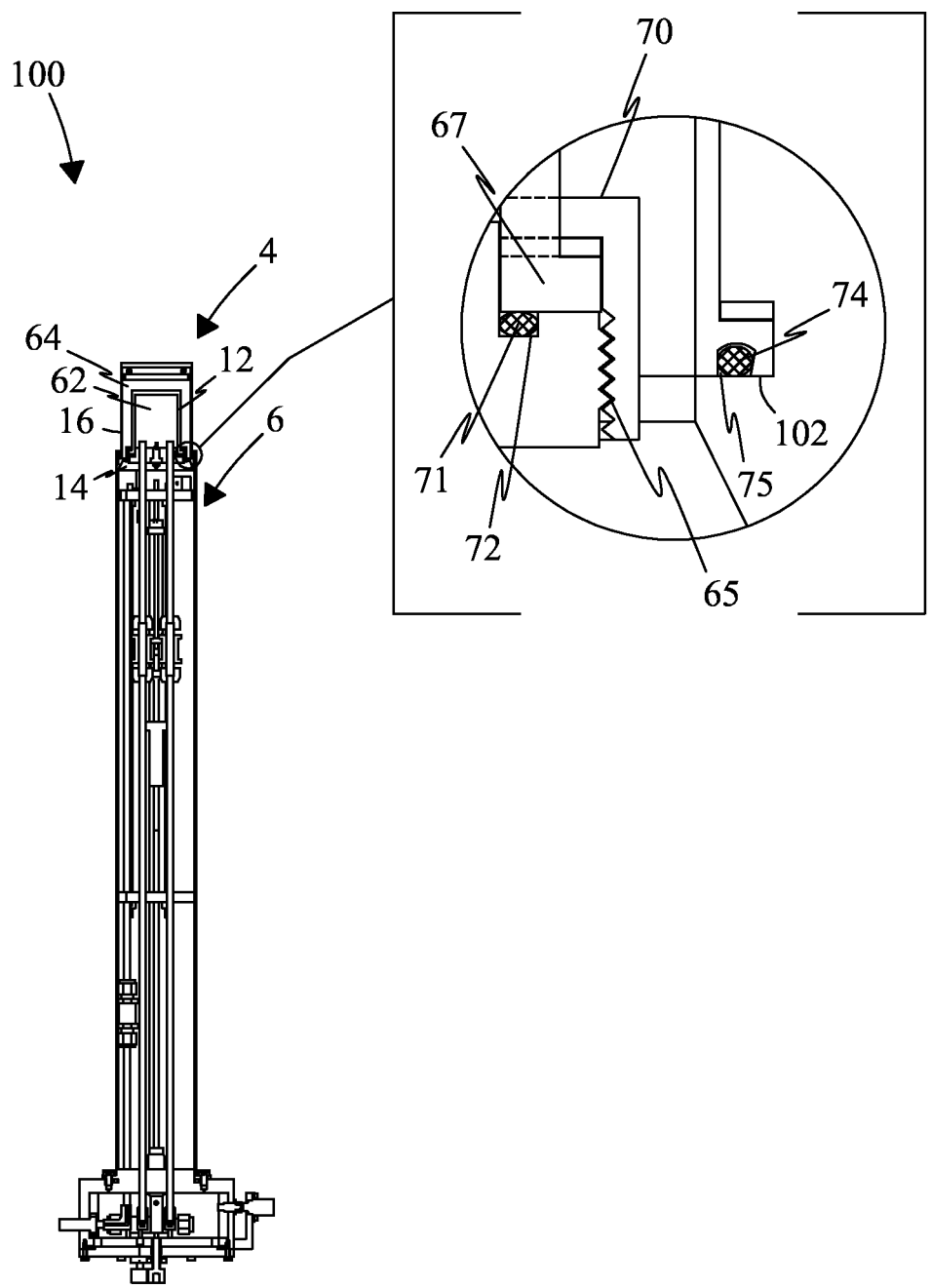

FIG. 4C presents an expanded cutaway side view showing O-rings positioned between upper module 4 and lower module 6 that seal inner containment volume 62 and outer containment volume 64 in the assembled and sealed MAS-NMR probe 100. As described previously in reference to FIG. 2B, inner enclosure 12 when secured to base platform 14 forms and seals an inner containment volume 62 within upper module 4. Inner enclosure 12 may be constructed, e.g., of polycarbonate and secured to the base platform 14 immediately above lower module 6. A threaded brass collar 70 screws onto inner threads 65 that circumvolve base platform 14 over the top of a flange 67 located at the base end of inner enclosure 12. When brass collar 70 is secured into position, flange 67 compresses a crush O-ring (seal) 71 seated in a groove 72 on base platform 14, which seals inner containment volume 62 within inner enclosure 12. Outer enclosure 16 with its conducting shielding when secured to probe body 2 over the top of inner enclosure 12 forms a secondary containment volume 64, which prevents release of sample particulates from inner enclosure 12.

In the expanded figure, a joint 102 is formed between upper module 4 and lower module 6 when outer enclosure 16 is secured to base platform 14. Outer enclosure 16 may be similarly secured to base platform 14 with a threaded brass ring 76 that screws onto threads 66 positioned on a lower exterior surface of base platform 14 over the top of a flange 73 positioned at the base end of outer enclosure 16. When brass ring 76 is screwed into position onto base platform 14, flange 73 compresses a crush O-ring 74 seated in a groove 75 on base platform 14, which seals outer containment volume 64 within outer enclosure 16, providing secondary containment that prevents release of hazardous sample materials from inner enclosure 12 to the exterior environment.

Figure 4D:
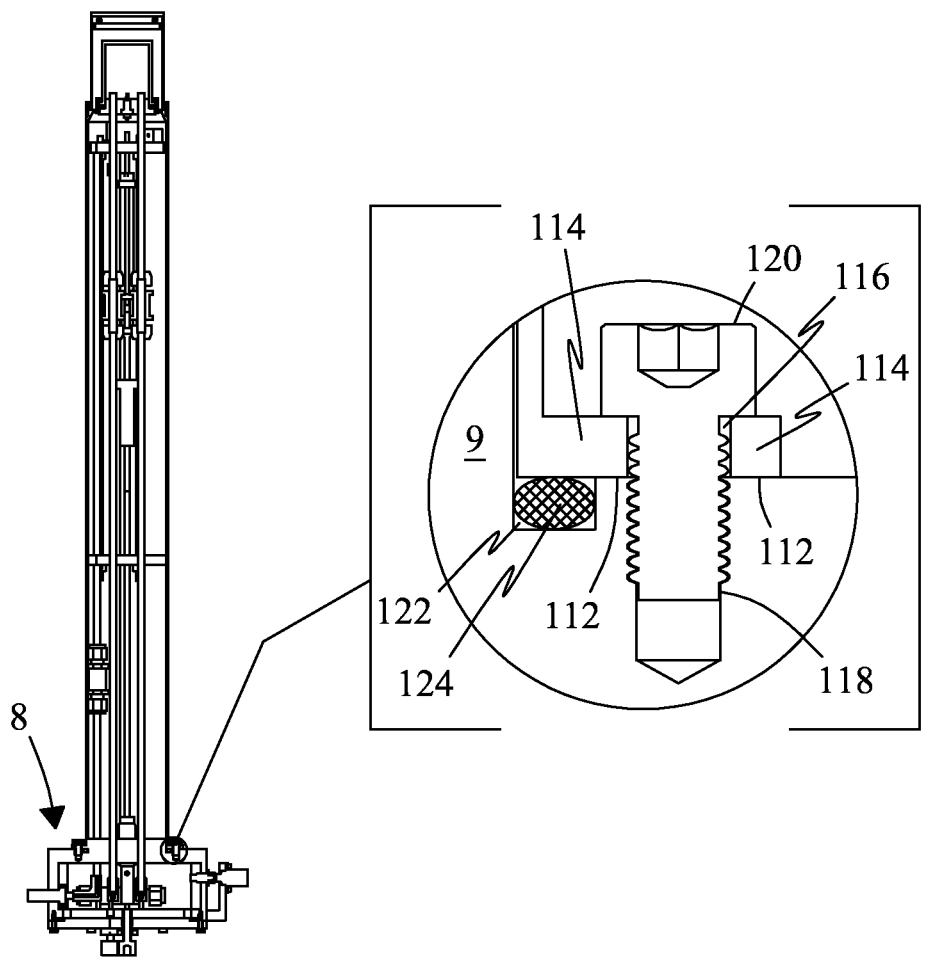

FIG. 4D presents an expanded cutaway side view showing O-rings positioned to seal the bottom end of lower module 6 and the top end of probe base 8 in the assembled and sealed MAS-NMR probe 100. In the expanded figure, a joint 112 may be formed between the outer shielding 2 of lower module 6 and cover 9 of probe base 8. Shielding 2 of lower module 6 may include a flange 114 with threaded (e.g., four) holes 116 positioned, e.g., 90° apart at a bottom end of shielding 2 of lower module 6 that align with threaded holes 118 positioned in cover 9 of probe base 8. Machine screws 120 insert and thread through threaded holes 116 of shielding 2 and threaded holes of 118 cover 9 to securely attach shielding 2 of lower module 6 to probe base 8. A circular groove 122 positioned in cover 9 of probe base 8 may include a diameter dimension that is smaller than those of screw holes 116 or 118 so as to secure a crush O-ring 124 that seals joint 112 positioned between flange 114 and probe base 8 when screws 120 are tightened.

Figure 4E:
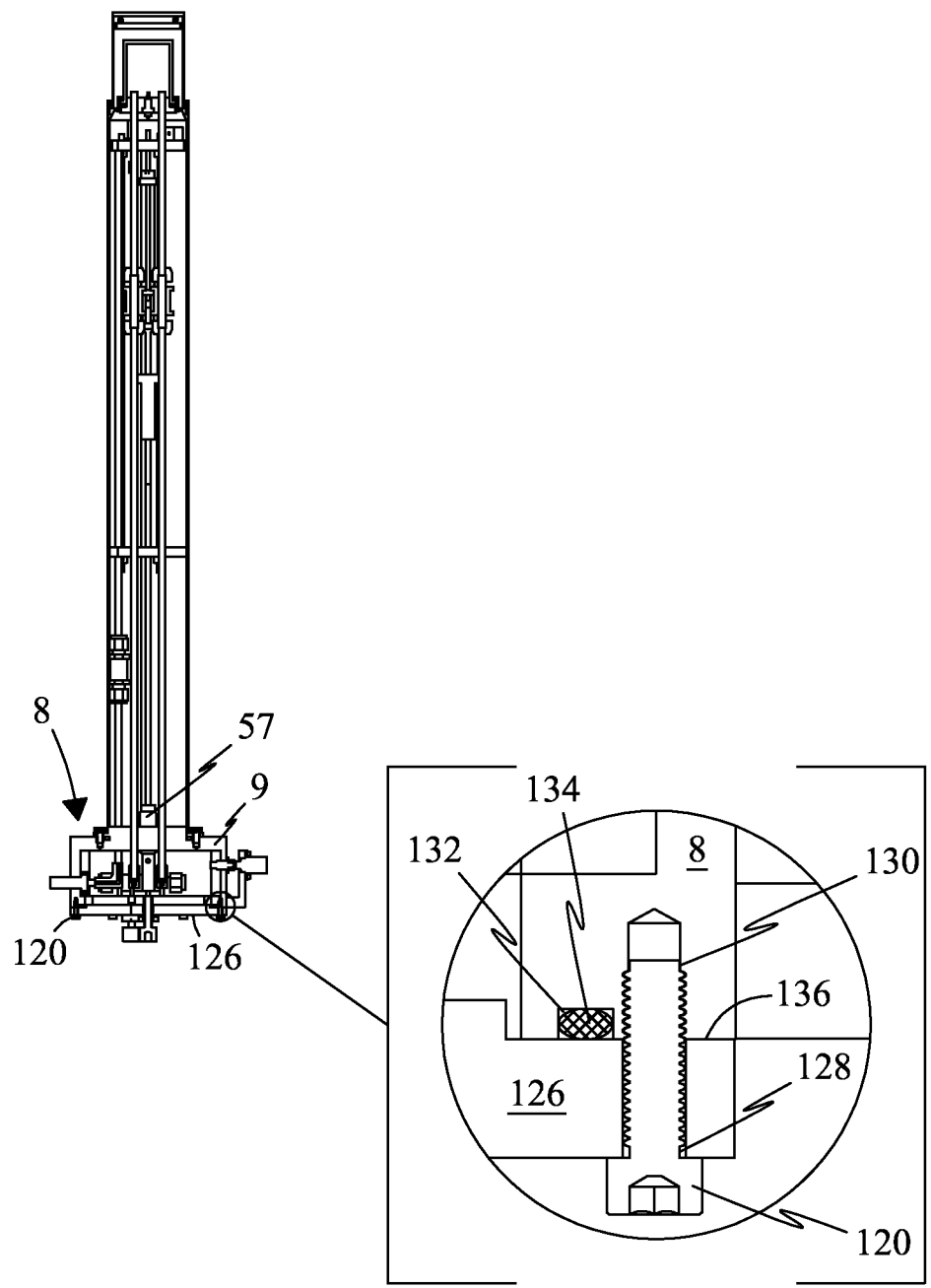

FIG. 4E presents an expanded cutaway side view showing attachment of a bottom cover 126 to the bottom of probe base 8. Bottom cover 126 may be in the form of an aluminum plate that is sized to match the area dimensions of probe base 8. A number of threaded holes 128 drilled around the perimeter of probe base 8 align with threaded holes 130 drilled vertically into walls of probe base 8. A groove 132 introduced in the bottom aluminum cover plate 126 of probe base 8 seats a crush O-ring 134 that seals joint 136 between bottom cover plate 126 and probe base 8 when machine screws 120 are tightened.

Figure 4F:
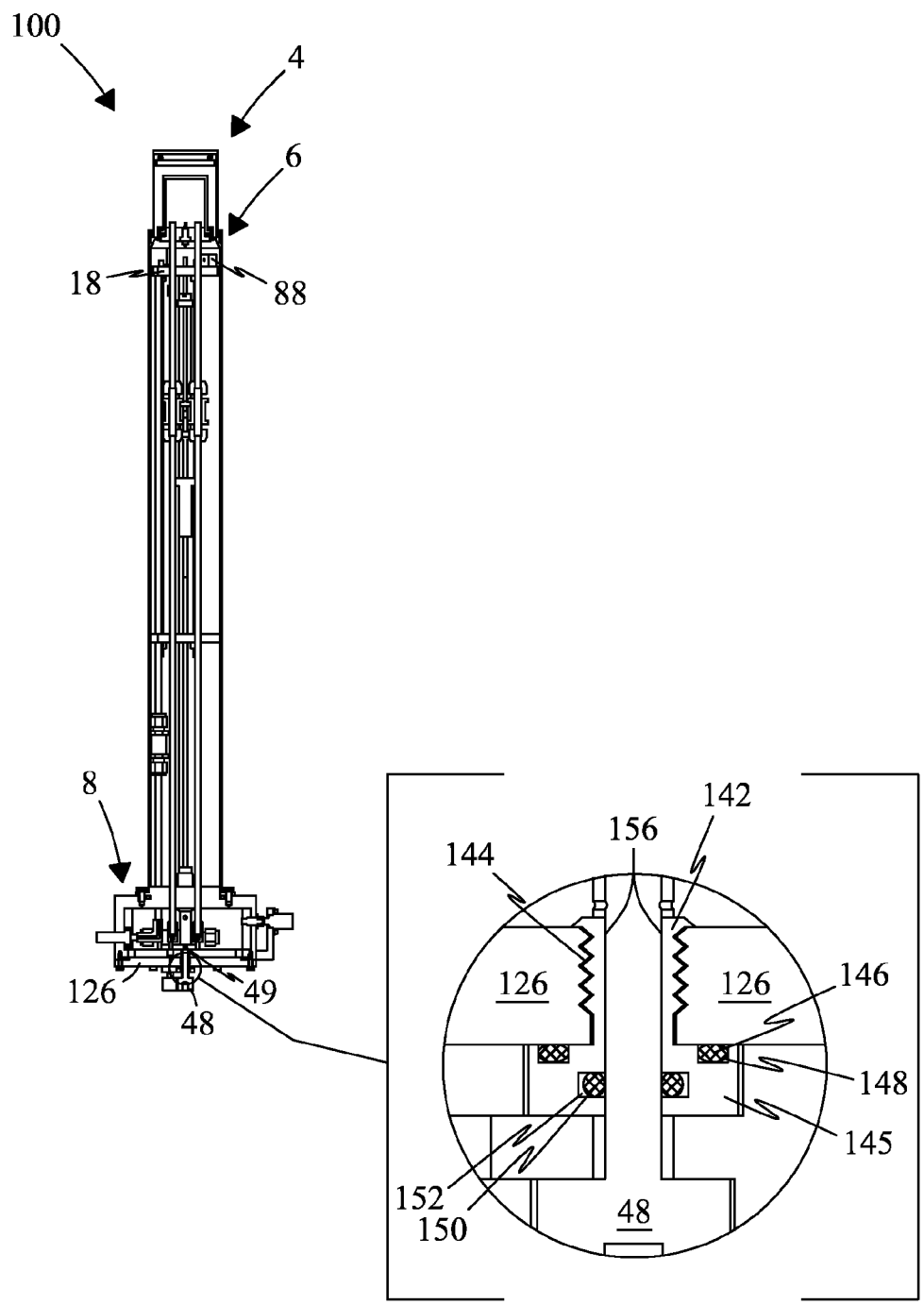

FIG. 4F shows an expanded cutaway view of O-ring seal 150 positioned around the tuning rod adjustment knob 48 that couples to the rotatable tuning rod 49. As described previously herein in reference to FIGS. 1A-1B, tuning rod 49 extends through a feed-through 57 positioned through top cover 9 of probe base 8 in lower module 6 and attaches to variable capacitors 88 (described previously in reference to FIG. 3) that are mounted to radiofrequency platform 18 (described previously in reference to FIG. 3) in lower module 6. Tuning rod adjustment knob 48 may enter into probe base 8 through an exteriorly threaded, cylindrical grommet 142 made of a thin metal or other suitable material that includes a round inner hole (not shown) at the center of the cylindrical grommet 142. Grommet 142 may include a collared or flared end 145 that keeps the grommet in place when screwed into its position in bottom cover plate 126 of probe base 8. An O-ring seal 146 may be seated in a circular groove 148 positioned into the surface of the grommet's flared end 145 immediately below bottom cover 126 of probe base 8. When grommet 142 is screwed into bottom cover 126 of probe base 8, O-ring 146 compresses and forms a seal that prevents air leakage through grommet threads 144. A second O-ring seal 150 may be seated in a groove 152 positioned radially around the grommet 142 to seals a joint 154 between tuning rod adjustment knob 48 when introduced through the center bore (not shown) of grommet 142 while allowing rotation when coupled to tuning rod 49.

Applications

The MAS-NMR probe of the present invention may be employed to analyze various hazardous and non-hazardous sample materials for applications where sample dispersal is not desirable. Only the upper module of the MAS-NMR probe containing the sample needs to be housed within a contamination area or glove box. The sealed MAS-NMR probe may also be employed in applications requiring inert atmospheres during operation.

Hazardous Samples

Hazardous sample materials include, but are not limited to, e.g., radioactive materials, hazardous chemicals including solids and semi-solids, and hazardous biological materials including solids and semi-solids.

Leak Testing

Integrity of the sealing components within MAS NMR probe 100 may be tested prior to operation, e.g., by blowing a fluorescent powder (e.g., Red Fluorescent Fingerprint Powder 6100, Lynn Peavey Company, Lenexa, Kans., USA) into the upper module (probe head) described previously in reference to FIGS. 1A-1B with a high-pressure gas, and then surveying the probe head with an ultraviolet light source to identify any potential leak sites, which ensures a proper seal is obtained within stator assembly (FIG. 2A) prior to use.

Loading and Sealing of Hazardous Samples

Figure 5:
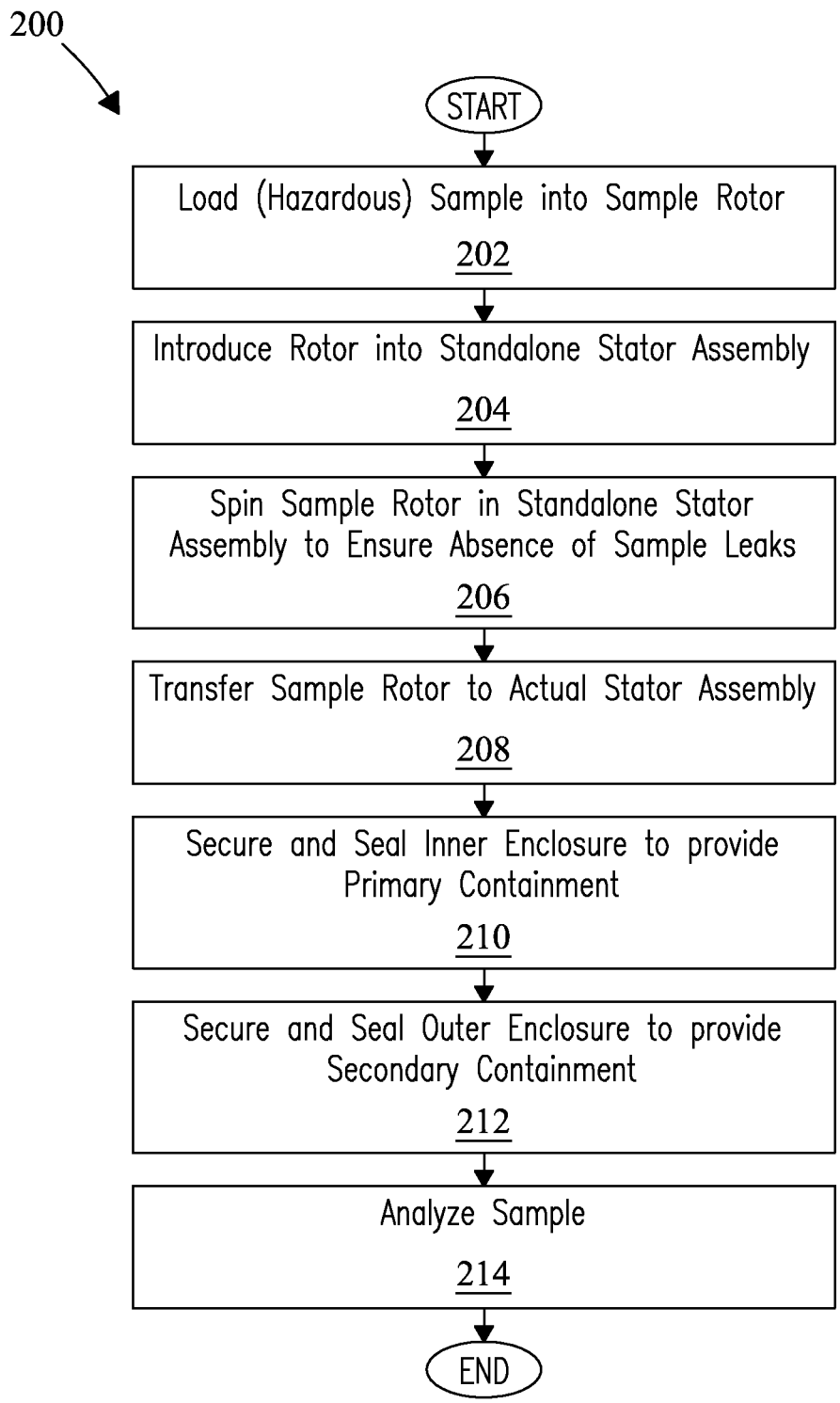
FIG. 5 lists exemplary steps for loading and sealing samples within the present invention.

FIG. 5 lists an exemplary process 200 for loading and sealing samples within the inner enclosure of the upper module of probe 100 for analysis. While exemplary steps are described, the process can include fewer or additional steps depending on the operator or the procedure. Indeed, all steps as will be envisioned by those of ordinary skill in the art in view of this disclosure are within the scope of the invention. No limitations are intended. {START}. In a first step {202}, a hazardous sample may be loaded into a sample rotor (e.g., a 3.2 mm rotor, Revolution NMR, Fort Collins, Colo., USA) (not shown) and sealed therein. Next {204}, after loading the sample into the sample rotor, the rotor may be introduced into a standalone test stage assembly within a test stage positioned, e.g., within a contamination fume hood or other controlled environment. Next {206}, the rotor may be spun in the test stage standalone stator assembly within the controlled environment to ensure that the rotor does not leak and that the rotor spins and performs properly before installing the rotor into the actual MAS-NMR sample probe for analyses. Then {208}, the rotor containing the hazardous sample may be transferred to the actual stator assembly within the actual MAS NMR probe. Next {210}, the inner enclosure may be threaded and secured to the base platform to form a primary containment seal within the inner enclosure. Then {212}, the outer enclosure may be threaded and secured to the base platform to form a secondary containment seal within outer enclosure within the MAS NMR probe. Then {214}, the sample may be analyzed to provide MAS NMR data. {END}.

While a number of embodiments of the present invention have been shown and described, it will be apparent to those skilled in the art that many changes and modifications may be made without departing from the invention in its broader aspects. The appended claims are therefore intended to cover all such changes and modifications as fall within the spirit and scope of the invention.

What is claimed is:

1. A sealable Magic Angle Spinning (MAS) Nuclear Magnetic Resonance (NMR) probe, comprising:
    an electrically shielded probe body having an inner enclosure that defines a first containment volume and is releasably sealed by selective compressive engagement of a sealing device to a base platform, the inner enclosure configured to enclose a stator assembly that receives a rotor containing a sample therein; and
    an outer enclosure that defines a second containment volume therein, and is adaptably sealable by secured connection to the probe body the outer enclosure when secured to the probe body covers the inner enclosure preventing release of the sample materials in the event of a breach in the inner enclosure or release of the sample materials within the MAS NMR probe.

2. The probe of claim 1, wherein the inner enclosure further comprises a first gas conduit configured to deliver a high-pressure bearing gas into the inner enclosure and a second conduit configured to deliver a high-pressure spin gas through the base platform into the inner enclosure to allow for operation of the stator assembly therein when the inner enclosure is sealed.

3. The probe of claim 2, wherein the first and second gas delivery conduits are coupled to one or more in-line check valves configured to prevent release of sample particulates.

4. The probe of claim 1, wherein the inner enclosure includes at least one exhaust gas conduit configured to release high-pressure exhaust gas from the stator assembly through the base platform in the upper module with a capacity that preserves the spin speed of the stator assembly during operation without releasing containment when the inner enclosure is sealed.

5. The probe of claim 4, wherein the at least one exhaust gas conduit is coupled to at least one particulate filter that is configured to remove sample particulates from the exhaust gas in the event of a release of sample particulates from the inner enclosure.

6. The probe of claim 1, wherein the outer enclosure includes a removable containment cap comprised of a transparent polycarbonate.

7. The probe of claim 1, wherein the inner enclosure is comprised of a transparent polycarbonate so as to allow viewing of the stator assembly within the first containment volume defined by the inner enclosure.

8. The probe of claim 1, further comprising at least one tuning circuit electrically coupled to the stator assembly to provide tuning of resonant frequencies during operation of the probe.

9. A method for performing MAS NMR analysis, comprising:
    introducing a rotor containing a sample into an electrically shielded probe body having an inner enclosure that defines a first containment volume and is adaptably sealable by secured connection to a base platform; the inner enclosure configured to enclose a stator assembly that receives the rotor containing the sample therein, the electrically shielded probe body also having an outer enclosure that defines a second volume therein, and is adaptably sealable by secured connection to the probe body;
    sealing the inner enclosure containing the stator assembly by securing the inner enclosure to the base platform disposed beneath the inner enclosure to form a first containment volume within the inner enclosure;
    sealing the outer enclosure by securing the outer enclosure to the probe body to form a secondary containment volume within the outer enclosure to prevent release of sample particulates in the event of a breach in the rotor or the inner enclosure within the probe during operation; and spinning the rotor in the stator assembly.

10. The method of claim 9, further including pre-spinning the rotor in a Contamination Area or other controlled environment located exterior to the probe to ensure the rotor containing the sample is properly sealed prior to introducing the sample into the MAS NMR probe for analysis therein.

11. The method of claim 9, wherein the sealing step includes mounting a collar over a flange disposed at the base end of the inner enclosure and threading the collar onto inner threads that circumvolve the base platform to compress a flexible sealing component that seals the inner enclosure and the primary containment volume therein that isolates the sample within the inner enclosure of the MAS NMR probe.

12. A Magic Angle Spinning (MAS) Nuclear Magnetic Resonance (NMR) probe for containment and isolation of a sample material during analysis, the probe comprising:

a modular probe body that includes a lower module and an upper module, the upper module comprised of an outer compartment and an inner compartment each defining sample containment volumes, the inner compartment defined by a polished polycarbonate housing that secures to a base of the probe body with a sealing collar that provides a gas-tight seal between the module and a base within the inner compartment of the probe body, whereby the base is separable from the rest of the probe body without breaching containment of the sample material from the inner compartment or the outer compartment;

the upper module further comprising:

a stator assembly coupled operatively to at least one gas inlet configured to introduce high pressure gases to the stator assembly in the inner compartment for rotation of the sample therein and at least one gas outlet to exhaust gasses from the inner compartment during operation of the NMR probe without breaching containment of material within the inner compartment.

13. The probe of claim 12, further comprising an antenna is electrically coupled to coaxial cables, capacitors, and inductors that define an RF electrical circuit that is tuned to selected frequencies during the NMR measurement.

14. The probe of claim 12, wherein the stator includes a fiber optic detector disposed to measure and regulate rotational speed of the MAS rotor during analysis of the sample material.

15. The probe of claim 12, wherein the lower module further includes gas delivery conduits that are coupled to one or more in-line particulate filters that retain sample particles therein in the event of gas backflow from the inner compartment during analysis of the sample material.

* * * * *